(12) United States Patent
Seppälä et al.

(10) Patent No.: US 8,550,070 B2
(45) Date of Patent: Oct. 8, 2013

(54) POWDER INHALER

(75) Inventors: Kari Seppälä, Helsinki (FI); Terhi Mattila, Kuopio (FI); Kalle Purma, Espoo (FI); Markku Härkönen, Tuusula (FI)

(73) Assignee: Orion Corporation, Espoo (FI)

( * ) Notice: Subject to any disclaimer, the term of this patent is extended or adjusted under 35 U.S.C. 154(b) by 1608 days.

(21) Appl. No.: 10/481,621

(22) PCT Filed: Jun. 20, 2002

(86) PCT No.: PCT/FI02/00545
§ 371 (c)(1),
(2), (4) Date: Aug. 12, 2004

(87) PCT Pub. No.: WO02/102444
PCT Pub. Date: Dec. 27, 2002

(65) Prior Publication Data
US 2005/0005933 A1 Jan. 13, 2005

(30) Foreign Application Priority Data
Jun. 20, 2001 (FI) .................................. 20011317

(51) Int. Cl.
*A61M 15/00* (2006.01)
(52) U.S. Cl.
USPC ............. 128/203.15; 128/203.19; 128/203.23
(58) Field of Classification Search
USPC ............. 128/200.23, 203.15, 203.19, 203.23
See application file for complete search history.

(56) References Cited

U.S. PATENT DOCUMENTS

| | | | |
|---|---|---|---|
| 2,587,215 A * | 2/1952 | Priestly | .................... 128/203.15 |
| 3,831,606 A | 8/1974 | Damani | |
| 3,874,381 A | 4/1975 | Baum | |
| 3,948,264 A | 4/1976 | Wilke et al. | |
| 4,200,099 A | 4/1980 | Guenzel et al. | |
| 4,206,758 A | 6/1980 | Hallworth et al. | |
| 4,240,418 A | 12/1980 | Rosskamp et al. | |
| 4,524,769 A | 6/1985 | Wetterlin | |
| 5,002,048 A | 3/1991 | Makiej | |
| 5,007,419 A | 4/1991 | Weinstein et al. | |

(Continued)

FOREIGN PATENT DOCUMENTS

| | | |
|---|---|---|
| CA | 2093809 | 2/1993 |
| EP | 1 106 196 A2 | 6/2001 |

(Continued)

OTHER PUBLICATIONS

U.S. Appl. No. 09/959,213, filed Jan. 16, 2002.

(Continued)

*Primary Examiner* — Clinton T Ostrup
(74) *Attorney, Agent, or Firm* — Finnegan, Henderson, Farabow, Garrett & Dunner, L.L.P.

(57) ABSTRACT

An inhaler device includes an air conduit including a mouthpiece and a dosing means adapted to provide a dose of powder to the air conduit for entrainment in the stream of air. In the area downstream from the dosing means the wall of the air conduit is provided with a secondary air inlet extending to the direction of the mouthpiece such that the entry of secondary air occurs over an extended length of the air conduit downstream from the dosing means.

14 Claims, 3 Drawing Sheets

(56) References Cited

U.S. PATENT DOCUMENTS

| | | |
|---|---|---|
| 5,070,870 A | 12/1991 | Pearce |
| 5,113,855 A * | 5/1992 | Newhouse ............... 128/203.12 |
| 5,161,524 A * | 11/1992 | Evans ...................... 128/203.15 |
| 5,169,029 A | 12/1992 | Behar et al. |
| 5,208,226 A | 5/1993 | Palmer |
| 5,239,993 A | 8/1993 | Evans |
| 5,301,666 A | 4/1994 | Lerk et al. |
| 5,327,883 A | 7/1994 | Williams et al. |
| 5,349,947 A | 9/1994 | Newhouse et al. |
| 5,383,850 A * | 1/1995 | Schwab et al. ................... 604/58 |
| 5,388,572 A | 2/1995 | Mulhauser et al. |
| 5,503,144 A * | 4/1996 | Bacon ..................... 128/203.15 |
| 5,507,281 A * | 4/1996 | Kuhnel et al. ............ 128/203.15 |
| 5,524,613 A | 6/1996 | Haber et al. |
| 5,533,502 A | 7/1996 | Piper |
| 5,575,280 A * | 11/1996 | Gupte et al. ............. 128/203.15 |
| 5,590,645 A | 1/1997 | Davies et al. |
| 5,617,845 A * | 4/1997 | Poss et al. ................ 128/203.15 |
| 5,664,557 A | 9/1997 | Makiej |
| 5,676,130 A | 10/1997 | Gupte et al. |
| 5,724,959 A | 3/1998 | McAughey et al. |
| 5,727,546 A | 3/1998 | Clarke et al. |
| 5,857,457 A | 1/1999 | Hyppola |
| 5,875,776 A | 3/1999 | Vaghefi |
| 5,881,719 A | 3/1999 | Gottenauer et al. |
| 5,904,139 A | 5/1999 | Hauswer |
| 5,941,241 A | 8/1999 | Weinstein et al. |
| 6,026,809 A | 2/2000 | Abrams et al. |
| 6,065,472 A | 5/2000 | Anderson et al. |
| 6,119,688 A | 9/2000 | Whaley et al. |
| 6,142,145 A | 11/2000 | Dagsland et al. |
| 6,182,655 B1 | 2/2001 | Keller et al. |
| 6,332,461 B1 | 12/2001 | Hyppola |
| 6,371,111 B1 | 4/2002 | Ohki et al. |
| 6,543,443 B1 | 4/2003 | Klimowicz et al. |
| 6,553,987 B1 | 4/2003 | Davies |
| 6,655,381 B2 | 12/2003 | Keane et al. |
| 6,769,601 B2 * | 8/2004 | Haikarainen et al. ....... 235/87 R |
| 6,810,874 B1 | 11/2004 | Koskela et al. |
| 6,983,748 B2 * | 1/2006 | Brown et al. ............ 128/203.15 |
| 6,990,976 B2 * | 1/2006 | Miyamoto ............... 128/200.23 |
| 2002/0033176 A1 * | 3/2002 | Casper et al. ............ 128/203.15 |
| 2003/0079743 A1 * | 5/2003 | Genova et al. ........... 128/203.12 |
| 2003/0116157 A1 | 6/2003 | Braithwaite et al. |
| 2003/0136406 A1 | 7/2003 | Seppala |
| 2004/0123865 A1 * | 7/2004 | Haikarainen et al. .... 128/203.15 |
| 2004/0255940 A1 * | 12/2004 | Pera ........................ 128/203.15 |

FOREIGN PATENT DOCUMENTS

| | | |
|---|---|---|
| GB | 2064334 | 6/1981 |
| GB | 2165159 | 4/1986 |
| WO | WO 92/00771 | 1/1992 |
| WO | WO 92/09322 | 6/1992 |
| WO | WO 94/06497 | 3/1994 |
| WO | WO 94/08552 | 4/1994 |
| WO | WO 94/11044 | 5/1994 |
| WO | WO 97/20589 | 6/1997 |
| WO | WO 97/25086 | 7/1997 |
| WO | WO 97/26934 | 7/1997 |
| WO | WO 97/40876 | 11/1997 |
| WO | WO 98/11929 | 3/1998 |
| WO | WO 98/26828 | 6/1998 |
| WO | WO 98/30262 | 7/1998 |
| WO | WO 99/07426 | 2/1999 |
| WO | WO 00/64519 | 11/2000 |
| WO | WO 00/64520 A1 * | 11/2000 |
| WO | WO 00/64779 | 11/2000 |
| WO | WO 02/34320 A1 | 5/2002 |

OTHER PUBLICATIONS

U.S. Appl. No. 10/399,913, filed Oct. 1, 2003.
Notice of Allowance from co-pending U.S. Appl. No. 09/959,213 dated Jun. 29, 2004.
Office Action from co-pending U.S. Appl. No. 09/959,213 dated May 11, 2004.
Office Action from co-pending U.S. Appl. No. 09/959,213 dated Aug. 15, 2003.
Office Action from co-pending U.S. Appl. No. 09/959,213 dated Dec. 18, 2002.
Notice of Allowance from co-pending U.S. Appl. No. 10/399,913 dated Jun. 14, 2005.
Office Action from co-pending U.S. Appl. No. 10/399,913 dated Nov. 9, 2004.

* cited by examiner

POWDER INHALER

This application is the U.S. national stage filing of international application no. PCT/FI02/00545, filed on Jun. 20, 2002, which claims the benefit of priority to Finnish patent application no. 20011317, filed on Jun. 20, 2001.

BACKGROUND OF THE INVENTION

The present invention relates to a device for dispensing of a powdered drug preparation by inhalation. In particular it relates to an inhaler device for aerosolizing a dose of powdered medicament for pulmonary delivery by inhalation. The device of the invention is useful, for example, in the treatment of asthma.

Several types of dry powder inhalers (DPIs) have been developed, in which the inhalation air of the patient is used for dispersing the drug particles. The powdered medicament is arranged as unit dose containers, e.g. blister packs, cartridges or peelable strips, which are opened in an opening station of the device. Alternatively, the unit dose is measured from a powder reservoir by means of a dosing member, e.g. a dosing cup.

Reservoir type powder inhalers comprising a medicament container and a dosing member for measuring and dispensing a unit dose are described e.g. in patent publications WO 92/00771 and WO 92/09322. In these devices, a series of dosing recesses are notched into the surface of a cylindrical or a conical metering member. When the metering member is rotated, the dosing recesses in turn will move first to a position in alignment with the powder container for being filled with a dose of powder falling from the powder container. Thereafter the filled dosing recess is moved to a position in alignment with the inhalation channel and the dose is inhaled directly from the dosing recess by a patient.

To increase flowability and dosing accuracy of the powdered medicament, the fine drug particles of respirable size are typically mixed with coarser carrier particles to form an ordered mixture, wherein fine drug particles are attached to the larger carrier particles. This technique complicates the powder aerosolization process and, in particular, necessitates the break-up of the drug/carrier agglomerates before they enter the patient's mouth and throat, where individual large particles and agglomerated large and small particles tend to deposit. Effective aerosolization and deagglomeration of the powder requires that forces exerted on particles (e.g. forces between particles and surfaces of the device, between drug particles and carrier particles or between drug particles themselves) must be overcome such that high fine particle dose (FPD) of particles in the respirable size range is obtained.

Various techniques have been used in DPIs to improve aerosolization and deagglomeration of drug powder during inhalation. These include turbines and impellers (U.S. Pat. Nos. 4,524,769 and 3,831,606) or other mechanical means (WO 98/26828), compressed gas (U.S. Pat. No. 5,349,947), cyclones (U.S. Pat. No. 5,301,666), electrostatic suspension or piezoelectric vibration (U.S. Pat. No. 3,948,264), venturis (WO 92/00771) and impactors (U.S. Pat. No. 5,724,959). In general, these DPIs have become more complicated and expensive.

DPIs having a spot-like secondary air inlet in the air channel are described in U.S. Pat. Nos. 2,587,215, 5,383,850, EP 1106196, WO 94/08552, WO 94/11044 and U.S. Pat. No. 5,113,855. However, such secondary air inlets are not adapted to provide efficient deagglomeration of the drug powder during inhalation.

Even though various DPIs have been described in the art, their ability to effectively aerosolize and deagglomerate the drug particles into a respirable particle size range is often limited or they use complicated techniques for increasing fine particle dose.

Thus, there is a need for a dry powder inhaler, which is simple but capable of providing more efficient aerosolization and deagglomeration of particles.

SUMMARY OF THE INVENTION

The present invention provides an inhaler for administering powder by inhalation, comprising an air conduit defined by a wall a stream of air being drawn through the air conduit upon inhalation by a user, the air conduit including a mouthpiece;

a dosing means adapted to provide a dose of powder to the air conduit for entrainment in the stream of air;

wherein in the area downstream from the dosing means the wall of the air conduit is provided with a secondary air inlet extending to the direction of the mouthpiece such that the entry of secondary air occurs over an extended length of the air conduit downstream from the dosing means.

It has been found that the amount of fine drug particles dispersed from an inhaler and entering deeply into the lungs can be significantly increased, if the air conduit wall, downstream from the dosing means, is equipped with a secondary air inlet which extends longitudinally along the air conduit wall. The secondary air inlet typically is a longitudinal slot in the air conduit wall, extending parallel to the longitudinal axis of the air conduit. The entry of secondary air provides additional turbulence at the area of air entry resulting in more efficient deagglomeration of particles. Furthermore, as the inlet of secondary air is designed to extend over a significant portion of the air conduit length downstream from the dosing means, the dispersed powder is subjected to powerful turbulence longer, preferably over the whole length of the air conduit between the dosing means and the outlet (mouthpiece). The longitudinal slot is preferably positioned adjacent to the dosing means.

DETAILED DESCRIPTION OF THE INVENTION

Figure 1:
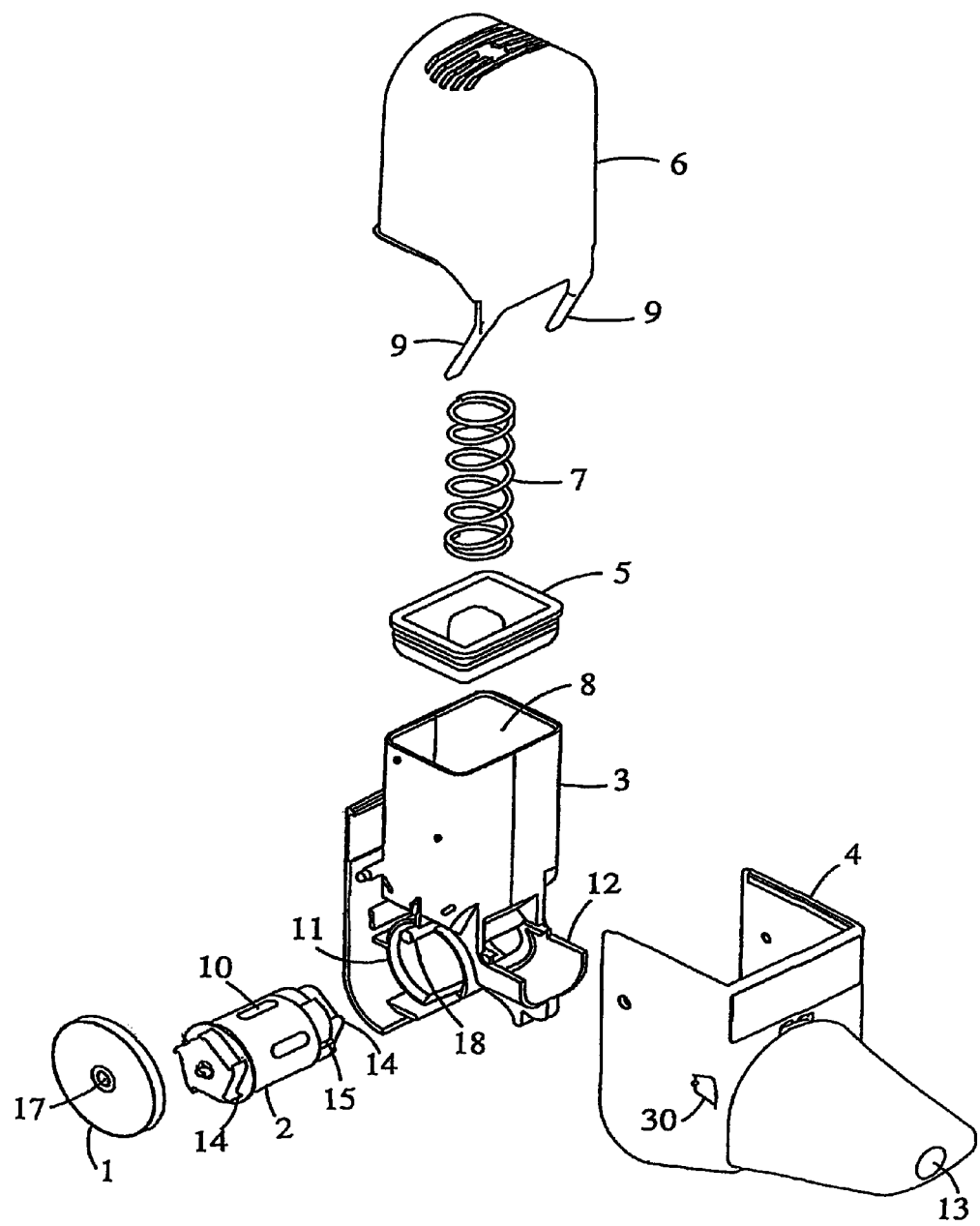
FIG. 1 is an explosive perspective view of the inhaler device according to one embodiment of the invention

The invention relates to an inhaler which comprises an air conduit defined by a wall, an air conduit including a mouthpiece and a dosing means adapted to provide a dose of powder to the air conduit for entrainment in the stream of air. At the area downstream from the dosing means the wall of the air conduit is provided with a secondary air inlet extending to the direction of the mouthpiece such that the entry of secondary air occurs over an extended length of the air conduit downstream from the dosing means.

Preferably, the inhaler is of multi-dose powder inhaler type, comprising a medicament container having a certain supply of medicament. Typically, the medicament container has a powder outlet in the form of an opening at the lower end.

The dosing means is suitably a manually movable dosing member, which can be in any suitable form for metering a dose of powder to the air conduit. Several forms of dosing members for multi-dose powder inhalers are known in the art, e.g. a rotatable dosing drum as described in e.g. WO 92/00771 and WO 92/09322, or a movable dosing slide as described in e.g. WO 95/31237 and WO 97/17097. Typically, at least one dosing recess is formed in the face of the dosing member for receiving a metered dose of the powdered medicament from medicament container. The face of the dosing member is adapted to be in contact with a similar mating face at the lower end of the medicament container. A dose of medicament powder is metered from the container, when the outlet of the container and the dosing recess of the dosing member are in alignment (the filling position).

The dosing member is suitably movable to another position for bringing the metered dose of the powdered medicament to the air conduit (the inhalation position). When a stream of air is inhaled through the air conduit via a mouthpiece, the dose of powdered medicament is dispersed in the inhaled air and into the lungs of the patient.

Preferably the dosing member is in the form of a drum or a slide. However, also other forms of dosing members can be used in the device of the invention.

The present invention is applicable in inhalers other than multi-dose powder inhalers, for example in unit dose powder inhalers. In unit dose powder inhalers the powdered medicament is arranged as unit dose containers, e.g. blister packs, cartridges or peelable strips, which are opened in an opening station of the device. In such case the dosing means consists simply of the deposit of the unit dose in the air conduit.

The air conduit defined by the air conduit wall has, downstream from the dosing means, suitably a substantially circular or elliptical cross section. The cross section can be constant or may vary.

The wall of the air conduit, in the area downstream from the dosing means, is provided with a secondary air inlet. The secondary air inlet extends to the direction of the mouthpiece along the air conduit wall such that the entry of secondary air occurs over an extended length of the air conduit.

Preferably the secondary air inlet is in the form of an elongate slot. Suitably the elongate slot extends substantially parallel to the longitudinal axis of the air conduit. Suitably the secondary air inlet, e.g. a elongate slot, covers at least 10%, preferably at least 20%, more preferably at least 30%, of the length of the air conduit downstream from the dosing means. The width of the slot is suitably about 1-60%, preferably about 5-40%, more preferably about 10-30%, of the inner diameter of the air conduit. In general, the slot should be dimensioned such that the portion of air conduit where strong turbulence occurs due to the entry of secondary air is as long as possible. On the other hand, the primary air stream responsible for aerosolizing the powder from the dosing means must be strong enough to effectively aerolize the powder from the dosing means to the inhaled air. For example, in case the secondary air inlet is an elongate slot, the slot may suitably begin at the vicinity of the dosing means and extend along the air conduit wall parallel to its axis a length which is about half of the total length of the air conduit downstream from the dosing means. Most preferably the elongate slot is positioned adjacent to the dosing means.

The air conduit wall can also be provided with more than one secondary air inlet. For example, the air conduit wall may be provided with two elongate slots. Such pair of slots may extend e.g. parallel and may be cut opposite to each other through the air conduit wall.

It is preferred that the secondary air inlet starts in the vicinity of the dosing means such that powerful turbulence occurs at the aerosolization area of the powder and continues as long as the powder is under the influence of secondary air entry.

Alternatively, the secondary air inlet is in the form of a series of openings, e.g. a series of circular openings. Such openings are preferably arranged along the air conduit wall to form a substantially straight line, which extends to the direction of the mouthpiece. The diameter of such openings are suitably about 1-60%, preferably about 5-40%, more preferably about 10-30%, of the inner diameter of the air conduit.

The device of the invention is further illustrated below by way of examples, with reference to FIGS. 1-3.

In FIG. 1 the structure of one embodiment of the device of the invention is shown in an explosive view. The main parts of the device are a body (3), a mouthpiece (4), a depressible cover (6), a metering drum (2) and a counter wheel (1). The body (3) defines a medicament container (8), which is to be filled with a powdered medicament. The container (8) has a square cross-section and a conical end portion. A lid (5) closes the upper edge of the medicament container. The depressible cover (6) together with a pair of elongate pawls (9), the function of which will be explained below, is adapted to cover the medicament container (6) and the lid (5). A spring (7) urges the depressible cover (6) in its upper (rest) position. A rotatable metering drum (2) having five dosing recesses (10) is mounted to the hollow cylindrical element (11), which is moulded together with the medicament container (8). Typically, the container has a supply of medicament for e.g. 200 doses.

The body (3) also defines the rear wall of the device as well as the projection (12) to receive the mouthpiece (4) including a cylindrical air conduit (13). The vertical walls of the mouthpiece serve as side walls of the device. On one vertical wall of the mouthpiece (4) a window (30) is provided through which part of the counter wheel (1) is visible.

The metering drum (2) has, in addition to the series of dosing recesses (10), two series of five ratchet teeth (14) adapted to engage with the elongate pawls (9) of the cover (6). The ratchet teeth (14) and the metering drum are molded as one-piece component. The device is actuated by pressing down the cover (6), whereby the pawls (9) engaging with the teeth (14) cause the metering drum (2) rotate so that rotation can only be accomplished stepwise corresponding to the peripheral distance between the dosing recesses (10). Furthermore, the cylindrical element (11) has an extended detent nose (not shown) adapted to engage with notches (15) in the metering drum (2) such that the rotation is possible only to one direction. The detent nose automatically aligns the dosing recesses (10) with the outlet of the medicament container (8) on the one side and the air channel (13) of the mouthpiece (4) on the other side.

A counter wheel (1) equipped with a central hole (17) is rotatably mounted on a bearing axle (18) extending from the body (3) of the inhaler.

Figure 2:
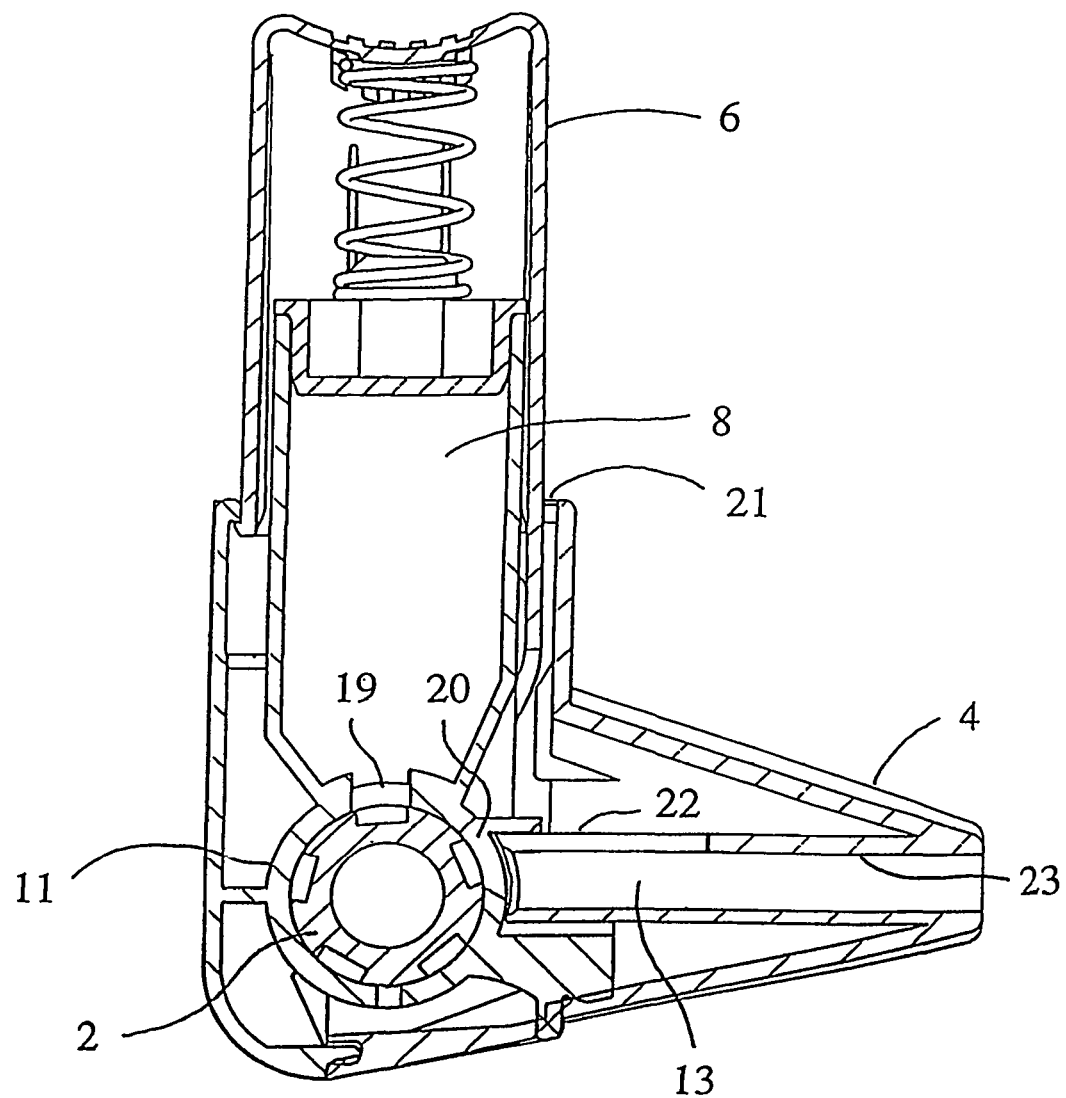
FIG. 2 is a longitudinal section of the device of FIG. 1 through the medicament container.

FIG. 2 shows a longitudinal section through the medicament container (8) of the device. The cylindrical body (11) has an opening (19) through which powder can fall from the medicament container (8) to the dosing recess (10) when the dosing recess is in alignment with the opening (19). Another opening (20) is provided at the level of the air conduit (13) for discharging the powder from the dosing recess to the air conduit (13) upon inhalation. In the position shown in FIG. 2 the upper dosing recess is just being filled with the dose of the powdered medicament from the medicament container (8), while the earlier filled dosing recess has turned to the air conduit (13) the dose being ready for inhalation. The mouthpiece (4), through which the powder can be inhaled, is formed at one side of the inhaler device and has an air conduit (13) for distribution of the dose of medicament from the dosing recess into the flow of breathing air. The air conduit (13) is defined, downstream from the metering drum (2), by an air conduit wall (23). The air conduit (13) is led through the mouthpiece (4) and finally forms an outlet, which is to be inserted in the mouth of the patient. In the area where the mouthpiece (4) is attached, air intakes (21) are provided. The intaken air is led to a slit formed between the opening (20) of the cylindrical element (11) and air conduit wall (23) of the mouthpiece (4). The slit provides strongly aligned primary air stream to the dosing recess to blow the powder out from the dosing recess into the air conduit (13).

The cylindrical air conduit wall (23) is provided with a secondary air inlet in the form of an elongate slot (22), which runs along the air conduit wall (23) parallel to the longitudinal axis of the air conduit (13). The slot (22) has a substantially constant width and is cut through the air conduit wall (23) perpendicularly to the longitudinal axis of the air conduit (13). The upstream end of the slot (22) is positioned just above the dosing cup and the downstream end of the slot (22) is in about halfway of the air conduit (13).

Figure 3:
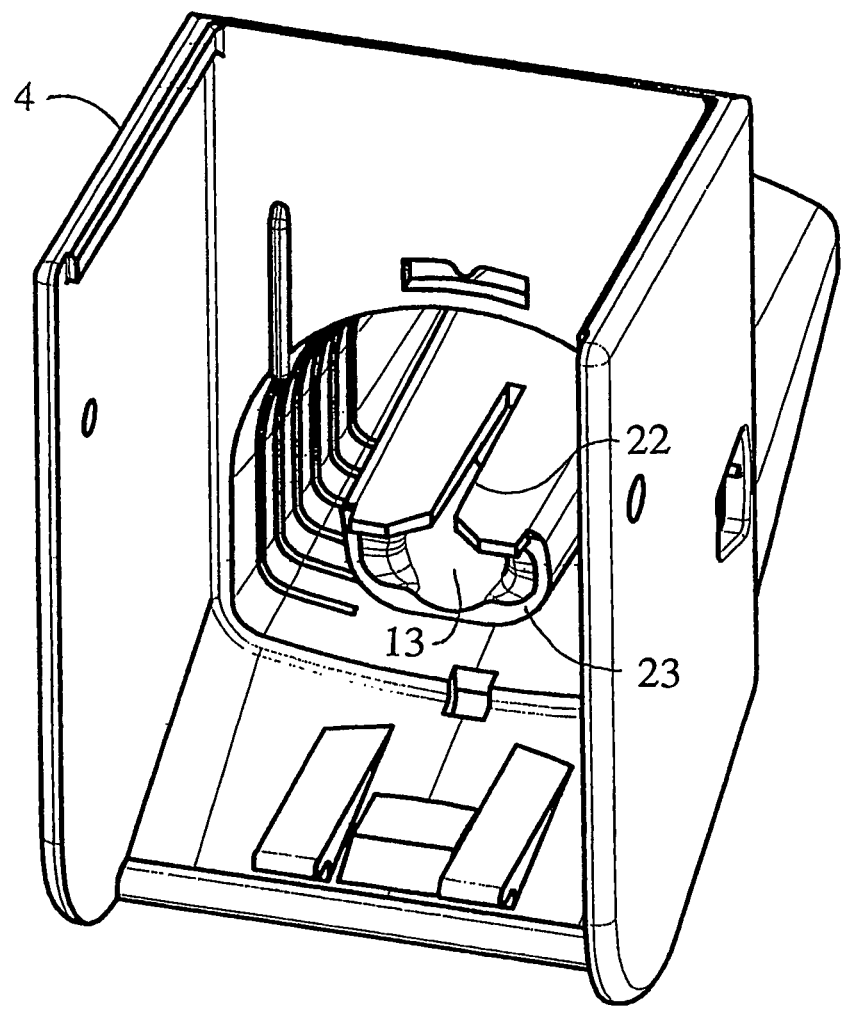
FIG. 3 is a perspective view of the mouthpiece including the air conduit downstream from the dosing means according to one embodiment of the invention.

FIG. 3 shows the mouthpiece (4) including the air conduit (13), the air conduit wall (23) and the slot (22) forming the secondary air inlet in a perspective view seen from the attachment side towards the outlet.

Those skilled in the art will recognize that modifications and variations can be made in form and detail to the disclosed embodiments without departing from the spirit and scope of the invention as defined in the following claims. It is considered to be routine for one skilled in the art to make such modifications to the device of the invention.

The invention claimed is:

1. An inhaler for administering powder by inhalation, comprising
   an air conduit having a wall;
   a mouthpiece;
   a dosing means adapted to provide a dose of powder to the air conduit;
   a primary air inlet for providing a stream of air adapted to disperse a dose of powder from the dosing means; and
   a secondary air inlet provided in the air conduit wall, wherein the secondary air inlet is positioned adjacent to and downstream from the dosing means and extends away from the dosing means along at least 20% of the air cohduit's length,
   whereby the powder dispersed from the dosing means is subjected to additional turbulence through the secondary air inlet.

2. An inhaler according to claim 1, wherein the secondary air inlet is in the form of an elongate slot.

3. An inhaler according to claim 2, wherein the width of the secondary air net is about 1-60% of the inner diameter of the air conduit.

4. An inhaler according to claim 2, wherein the length of the secondary air inlet is at least 30% of the length of the air conduit.

5. An inhaler according to claim 2, wherein the width of the secondary air inlet is about 5-40% of the inner diameter of the air conduit.

6. An inhaler according to claim 2, wherein the width of the secondary air inlet is about 10-30% of the inner diameter of the air conduit.

7. The inhaler according to claim 1, wherein the powder dispersed from the dosing means is subjected to additional turbulence along the length of the secondary air inlet.

8. An inhaler for administering powder by inhalation, comprising
   an air conduit having a wall;
   a mouthpiece;
   a dosing means adapted to provide a dose of powder to the air conduit;
   a primary air inlet for providing a stream of air adapted to disperse a dose of powder from the dosing means; and
   a secondary air inlet provided in the air conduit wall, wherein the secondary air inlet is downstream from the dosing means and extends away from the dosing means along at least 20% of the air conduit's length,
   whereby the powder dispersed from the dosing means is subjected to additional turbulence through the secondary air inlet.

9. An inhaler according to claim 8, wherein the secondary air inlet is adjacent to the dosing means.

10. An inhaler according to claim 8, wherein the secondary air inlet is in the form of an elongate slot.

11. An inhaler according to claim 10, wherein the width of the secondary air inlet is about 1-60% of the inner diameter of the air conduit.

12. An inhaler according to claim 10, wherein the width of the secondary air inlet is about 5-40% of the inner diameter of the air conduit.

13. An inhaler according to claim 10, wherein the width of the secondary air inlet is about 10-30% of the inner diameter of the air conduit.

14. An inhaler according to claim 8, wherein the length of the secondary air inlet is at least 30% of the length of the air conduit.

* * * * *